(12) United States Patent
Tseng et al.

(10) Patent No.: US 9,084,861 B2
(45) Date of Patent: Jul. 21, 2015

(54) ORAL POSITIONING DEVICE FOR POSITIONING BREATHING TUBE

(71) Applicants: Chung-Chih Tseng, Kaohsiung (TW); Yao-Te Peng, Kaohsiung (TW)

(72) Inventors: Chung-Chih Tseng, Kaohsiung (TW); Yao-Te Peng, Kaohsiung (TW)

(*) Notice: Subject to any disclaimer, the term of this patent is extended or adjusted under 35 U.S.C. 154(b) by 244 days.

(21) Appl. No.: 13/835,151

(22) Filed: Mar. 15, 2013

(65) Prior Publication Data
US 2014/0261460 A1    Sep. 18, 2014

(51) Int. Cl.
*A61C 5/14*    (2006.01)
*A61M 16/04*    (2006.01)

(52) U.S. Cl.
CPC ....... *A61M 16/0493* (2014.02); *A61M 16/0497* (2013.01)

(58) Field of Classification Search
CPC ................. A61M 16/0493; A61M 16/0497
USPC .............. 128/848, 859–862, 207.11, 207.14, 128/207.17, 205.25; 602/902; 433/6
See application file for complete search history.

(56) References Cited

U.S. PATENT DOCUMENTS

| 2,107,667 A * | 2/1938 | Hermson ...................... 36/128 |
| 4,664,109 A * | 5/1987 | Rasocha .................. 128/207.14 |
| 5,031,611 A * | 7/1991 | Moles ...................... 128/201.11 |
| 5,778,877 A * | 7/1998 | Stuart ..................... 128/207.17 |
| 2012/0125339 A1* | 5/2012 | Ho et al. .................. 128/205.25 |

FOREIGN PATENT DOCUMENTS

TW    M386898    8/2010

* cited by examiner

*Primary Examiner* — Michael Brown
(74) *Attorney, Agent, or Firm* — Muncy, Geissler, Olds & Lowe, P.C.

(57) ABSTRACT

An oral positioning device for positioning a breathing tube includes a first teeth guard having a first groove, and a first seat extends from the first teeth guard. The first seat has a first notch. An engaging member has two pivots and a second seat which is engaged with the first seat. The second seat has a second notch which is cooperated with the first notch to form a positioning hole which the breathing tube extends. A second teeth guard has a second groove and two pivotal holes with which the two pivots are pivotably engaged. The first and second seats position the breathing tube in the patient's mouth. The first and second teeth guards protect the patient's teeth from being damaged by of the laryngoscope when opening the patient's mouth.

7 Claims, 7 Drawing Sheets

ORAL POSITIONING DEVICE FOR POSITIONING BREATHING TUBE

FIELD OF THE INVENTION

The present invention relates to an oral positioning device, and more particularly, to an oral positioning device for positioning a breathing tube and protecting the teeth of a patient so as to avoid the incisors of the patient from being damage or broken when using the laryngoscope to force the patient's mouth open.

BACKGROUND OF THE INVENTION

When applying an emergency intubation to a patient, the doctor uses a laryngoscope to force the mouth of the patient open and inserts a breathing tube into the body of the patient. However, in order to quickly send the breathing tube into the patient's body, unexpected impact may happen such as the incisors may be broken by the equipment, and the patient has to receive dental implant or denture.

Taiwan Utility Model No. M386898 discloses a positioning device for an inner tube of a breathing tube and comprises an adjustable clamp and a strap. The adjustable clamp has a first clamp unit having a first clamping portion, and a second clamp has a second clamping portion. The first and second clamping portions are correspondingly connected so as to retain the inner tube. An adjusting unit has a resilient member connected between the first and second clamp units so as to adjust the relationship between the first and second clamping portions. An anti-bite structure is formed at one side of the first clamping portion and has a reception portion for mounting to and covering the inner tube so as to protect the inner tube. The strap is connected between the two respective sides of the first clamp unit.

Nevertheless, when using the laryngoscope to open the patient's mouth, the above mentioned device does not protect the teeth of the patient, and the patient's incisors may be broken or damaged by improper treatment, such as unintentionally applying an overloading force, from the doctor or the medical staff.

The present invention intends to provide an oral positioning device to protect the incisors of patient.

SUMMARY OF THE INVENTION

The present invention relates to an oral positioning device for positioning a breathing tube and comprises at least one teeth guard having a through hole through which the breathing tube extends. A diameter of the through hole is configured to be larger than a diameter of the breathing tube.

Preferably, the at least one teeth guard has at least one groove defined therein.

Alternatively, the present invention provides an oral positioning device for positioning a breathing tube and comprises a first teeth guard, an engaging member and a second teeth guard. The first teeth guard has a first groove and a first seat extends from the first teeth guard. The first seat has a first notch. An engaging member has two pivots on two sides thereof. The engaging member has a second seat which is engaged with the first seat. The second seat has a second notch which is cooperated with the first notch to form a positioning hole so that the breathing tube extends therethrough. A second teeth guard has a second groove and two pivotal holes, wherein the two pivots are pivotably engaged with the two pivotal holes.

Preferably, the first seat comprises two protrusions extending therefrom and a plate extending therefrom and located between the two protrusions. The first notch is formed on the plate. An engaging part is defined between the protrusions and the plate. The second seat has two engaging protrusions extending therefrom, the two engaging protrusions are engaged with the engaging part.

Preferably, the first teeth guard has multiple first guide members, and a first guide passage is defined between any two of the adjacent first guide members. The second teeth guard has multiple second guide members and a second guide passage is defined between any two of the adjacent second guide members.

Preferably, the first seat of the first teeth guard has a first engaging portion. The second seat of the engaging member has two engaging protrusions. Each of the two engaging protrusions has a second engaging portion which is engaged with the first engaging portion.

Preferably, the first engaging portion is a protruding part which is located the outside of the first teeth guard, and the second engaging portion is a hole.

One aspect of the present invention is to provide an oral positioning device which has grooves to accommodate the patient's teeth, and the elastic teeth guard protects the incisors of patient when using the laryngoscope.

Another aspect of the present invention is that when the breathing tube is inserted into the patient's body, the engaging member is connected between the first and second teeth guards to position the breathing tube and prevent the breathing tube from dropping/disengaging from the patient's mouth.

The present invention will become more obvious from the following description when taken in connection with the accompanying drawings which show, for purposes of illustration only, a preferred embodiment in accordance with the present invention.

DETAILED DESCRIPTION OF THE PREFERRED EMBODIMENT

Figure 1:
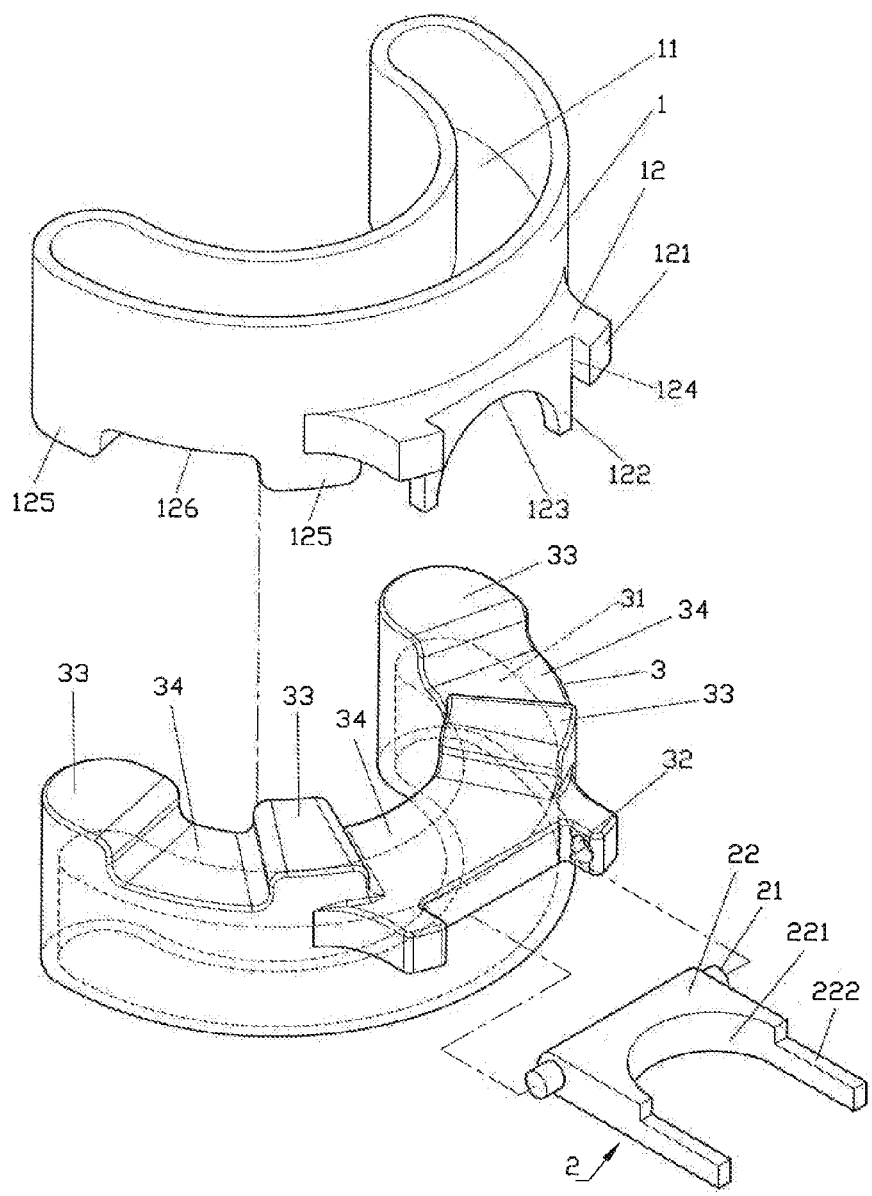
FIG. 1 is an exploded view to show the oral positioning device of the present invention.
Figure 2:
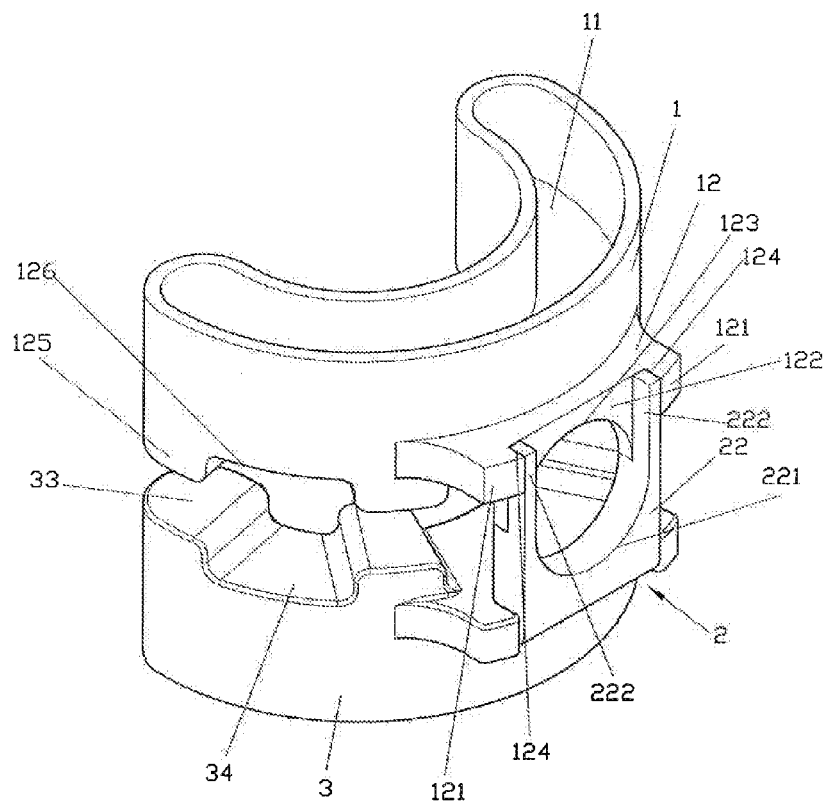
FIG. 2 is a perspective view to show the oral positioning device of the present invention.

Referring to FIGS. 1 and 2, the oral positioning device for positioning a breathing tube "A" (shown in FIGS. 4 and 5) of the present invention comprises a first teeth guard 1, an engaging member 2 and a second teeth guard 3.

The first teeth guard 1 has a first groove 11 and a first seat 12 extending from the first teeth guard 1. The first seat 12 comprises two protrusions 121 extending therefrom and a plate 122 extending therefrom and located between the two protrusions 121. A first notch 123 is formed on the plate 122. An engaging part 124 is defined between the protrusions 121 and the plate 122. The first teeth guard 1 has multiple first guide members 125, and a first guide passage 126 is defined between any two of the adjacent first guide members 125.

The engaging member 2 has two pivots 21 on two sides thereof. The engaging member 2 has a second seat 22 which is engaged with the first seat 12. The second seat 22 has a second notch 221 and two engaging protrusions 222 extending therefrom. The second notch 221 is defined between the second seat and the two engaging protrusions 222. The two engaging protrusions 222 are configured to be engaged with the engaging part 124.

The second teeth guard 3 has a second groove 31 and two pivotal holes 32 which the two pivots 21 are pivotably engaged with. The second teeth guard 3 has multiple second guide members 33 and a second guide passage 34 is defined between any two of the adjacent second guide members 33.

Figure 3:
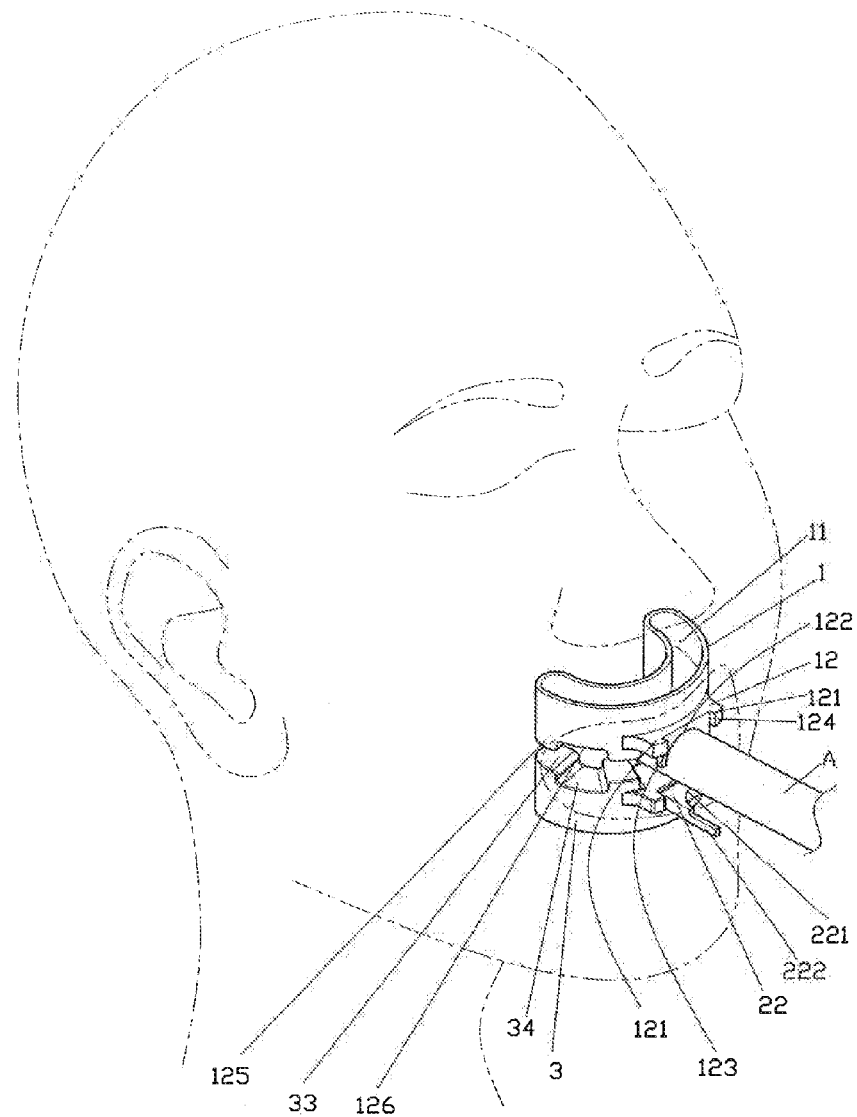
FIG. 3 shows the use of the breathing tube cooperated with the oral positioning device of the present invention.
Figure 4:
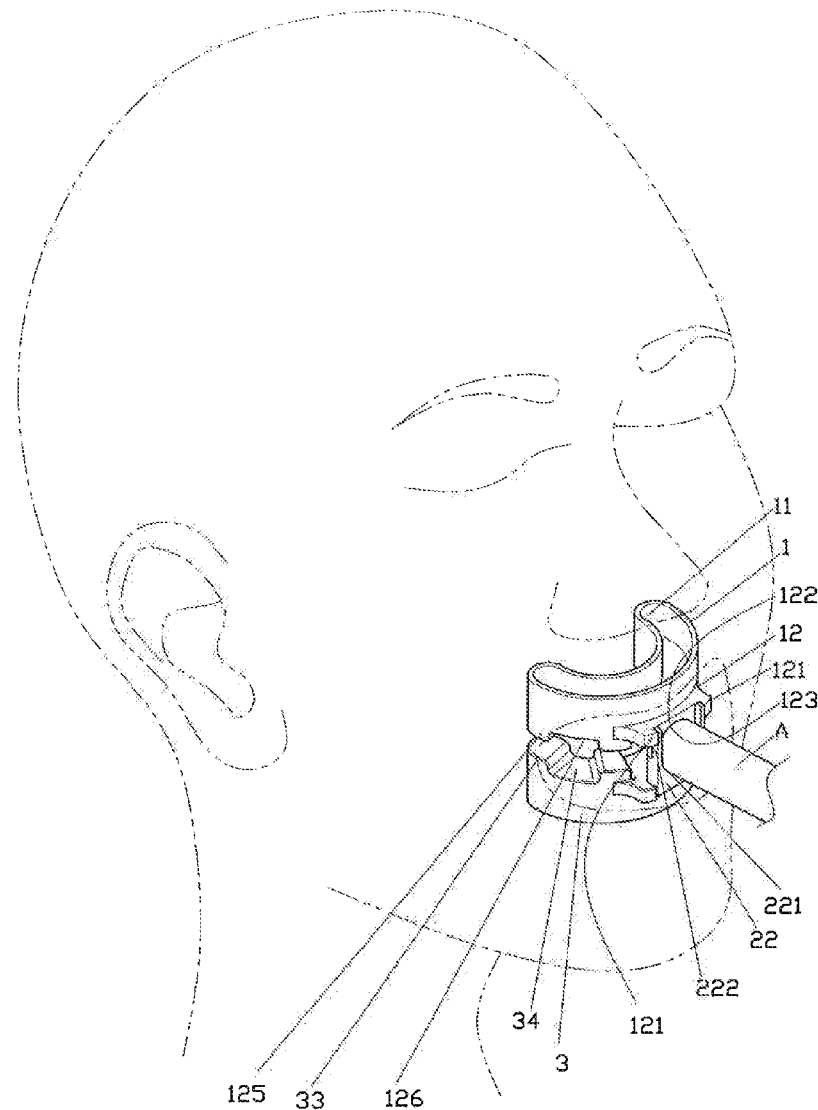
FIG. 4 shows that the breathing tube is positioned by the oral positioning device of the present invention.

When introducing the breathing tube "A" into the patient's body as shown in FIG. 3, the upper teeth are accommodated in the first groove 11 of the first teeth guard 1, and the bottom teeth are accommodated in the second groove 31 of the second teeth guard 3. Dental paste is optionally filled in the first and second grooves 11, 31, so that the patient can easily grip the first and the second teeth guards 1, 2 with their teeth much easily and firmly. The first and second teeth guards 1, 3 are made by medical grade plastic. The first guide members 125 and second guide members 33 define the first and second guide passages 126, 34 which are aligned to form guiding holes, so that other equipment can be inserted through the guiding holes of the first and second guide passages 126, 34. In this example, the laryngoscope (not shown) can be inserted into the mouth through the guiding hole, located between the first and second seats 12, 22 and defined by the first and second guide passages 126, 34, so as to open the mouth of the patient. The breathing tube "A" then extends through the hole and is introduced into the patient's body. As shown in FIG. 4, the pivots 21 of the engaging member 2 are pivotably engaged with the pivotal holes 32 of the second teeth guard 3, so that the engaging member 2 is pivoted to engage the engaging protrusions 222 with the engaging part 124, and the first and second notches 123 and 221 are cooperatedly configured to form a positioning hole. The breathing tube "A" is penetrated through the positioning hole and is positioned in the positioning hole between the first and second notches 123 and 221, so that the breathing tube "A" is not disengaged from the first and second teeth guards 1, 2. Preferably, the diameter of the positioning hole is smaller than the diameter of the breathing tube "A" so as to fastenly position the breathing tube "A" in the positioning hole. The first and second teeth guards 1, 2 also provide protection to the teeth of the patient when using the laryngoscope to open the patient's mouth.

Figure 5:
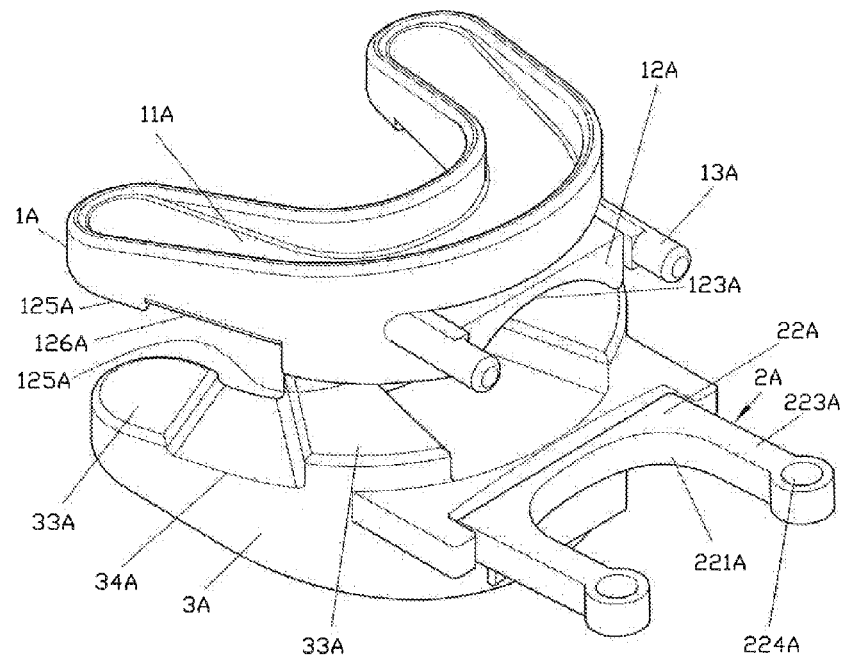
FIG. 5 is a perspective view to show the second embodiment of the oral positioning device of the present invention.
Figure 6:
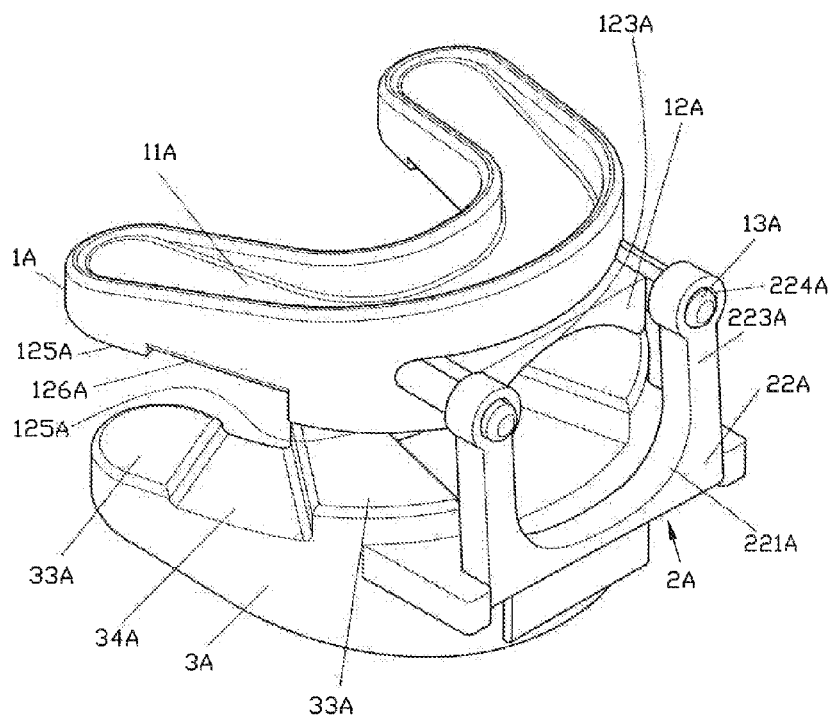
FIG. 6 is a perspective view to show the use of the second embodiment of the oral positioning device of the present invention, wherein the second engaging portions are engaged with the first engaging portions.

FIG. 5 shows the second embodiment of the present invention, wherein the first seat 12A of the first teeth guard 1A has two first engaging portions 13A, and the second seat 22A of the engaging member 2A has two engaging protrusions 223A. Each of the two engaging protrusions 223A has a second engaging portion 224A which is engaged with the first engaging portion 13A. Each of the two first engaging portions 13A is a protruding part located on outside of the first teeth guard 1A, and each the two second engaging portion 224A is configured as a hole in which the first engaging portion 13A is installed. A first notch 123A is formed between the two first engaging portions 13A, and a second notch 221A is formed between the two engaging protrusions 223A. As shown in FIG. 6, the user may pivot the engaging member 2A to engage the second engaging portion 224A of the engaging protrusions 223A with the first engaging portion 13A. The breathing tube "A" (not shown) can be positioned between a positioning hole which is formed by the first and second notches 123A, 221A. The first groove 11A, the first guide members 125A, the first guide passages 126A, the second guide members 33A and the second guide passages 34A are the same as those in the previous embodiment.

Figure 7:
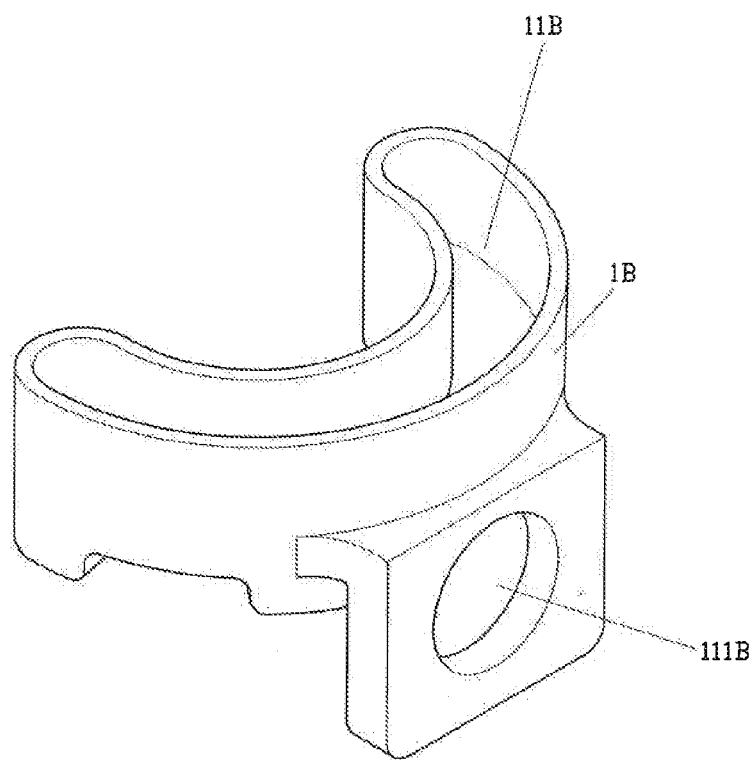
FIG. 7 is a perspective view to show the third embodiment of the oral positioning device of the present invention.

FIG. 7 shows the third embodiment of the present invention, wherein the oral positioning device for positioning a breathing tube "A" of the present invention comprises at least one first teeth guard 1B. The at least one first teeth guard 1B has at least one groove 11B and a through hole 111B which is configured to allow the breathing tube to extend therethrough. The diameter of the through hole 111B is larger than the diameter of the breathing tube "A".

While we have shown and described the embodiment in accordance with the present invention, it should be clear to those skilled in the art that further embodiments may be made without departing from the scope of the present invention.

What is claimed is:

1. An oral positioning device for positioning a breathing tube, comprising:
   a first teeth guard having a first groove and a first seat extending from the first teeth guard, the first seat having a first notch;
   an engaging member having two pivots on two sides thereof, the engaging member having a second seat which is engaged with the first seat, the second seat having a second notch which is cooperated with the first notch to form a positioning hole which is configured to allow the breathing tube to extend therethrough, and
   a second teeth guard having a second groove and two pivotal holes, the two pivots being pivotably engaged with the two pivotal holes.

2. The device as claimed in claim 1, wherein the first seat comprises two protrusions extending therefrom and a plate extending therefrom and located between the two protrusions, the first notch is form on the plate, an engaging part is defined between the two protrusions and the plate, the second seat has two engaging protrusions extending therefrom, the two engaging protrusions are engaged with the engaging part.

3. The device as claimed in claim 1, wherein the first teeth guard has multiple first guide members, and a first guide passage is defined between any two of the adjacent first guide members, the second teeth guard has multiple second guide members and a second guide passage is defined between any two of the adjacent second guide members.

4. The device as claimed in claim 3, wherein the first seat of the first teeth guard has a first engaging portion, the second seat of the engaging member has two engaging protrusions, each of the two engaging protrusions has a second engaging portion which is engaged with the first engaging portion.

5. The device as claimed in claim 4, wherein each of the two first engaging portions is a protruding part located on outside of the first teeth guard, and each of the two second engaging portions is a hole.

6. The device as claimed in claim 1, wherein the first seat of the first teeth guard has a first engaging portion, the second seat of the engaging member has two engaging protrusions, each of the two engaging protrusions has a second engaging portion which is engaged with the first engaging portion.

7. The device as claimed in claim 6, wherein each of the two first engaging portions is a protruding part located on outside of the first teeth guard, and each of the two second engaging portions is a hole.

* * * * *